United States Patent [19]

Jasper, Jr.

[11] Patent Number: 4,674,513
[45] Date of Patent: Jun. 23, 1987

[54] ACTIVE MICROWAVE CAVITY FOR ELECTRON PARAMAGNETIC RESONANCE (EPR) APPARATUS

[76] Inventor: Louis J. Jasper, Jr., 16 Wolley Way, Ocean, N.J. 07712

[21] Appl. No.: 783,992

[22] Filed: Oct. 4, 1985

[51] Int. Cl.⁴ .............................................. A61B 6/00
[52] U.S. Cl. .................................. 128/653; 324/316; 330/44
[58] Field of Search ............... 128/653, 804; 324/316; 330/44

[56] References Cited

U.S. PATENT DOCUMENTS

| | | | |
|---|---|---|---|
| 4,017,855 | 4/1977 | Buck et al. | 324/300 |
| 4,280,096 | 7/1981 | Karthe et al. | 324/316 |
| 4,593,248 | 6/1986 | Hyde et al. | 324/317 |

OTHER PUBLICATIONS

M. Bersohn and J. Bird, "Electron Paramagnetic Resonance," W. Benjamin Inc. (1966) pp. 201-207.

Primary Examiner—Kyle L. Howell
Assistant Examiner—Ruth S. Smith
Attorney, Agent, or Firm—Sheldon Kanars; Jeremiah G. Murray; John K. Mullarney

[57] ABSTRACT

This disclosure relates to a microwave amplifier (22) having an active X-Band microwave cavity (33) for use in electron paramagnetic resonance (EPR) measurements on large, lossy, irradiated, samples such as a human finger. The amplifier comprises an input section (31), a drift section (32) and an output section (33) which is the aforementioned active microwave cavity. An electron beam is used to input RF energy into the cavity. The input and output section have small helical couplers (34) for coupling RF energy onto and off of the electron beam. The RF wave is essentially "trapped" in the cavity because of the non-reciprocal nature of the electron beam medium and because the guide (i.e., drift section) at the input to the cavity has dimensions such that the frequency of the RF microwave energy is below the guides lower cut-off frequency. Also, a frequency "locking" effect occurs in the output cavity. The input frequency can be varied from 1-2% yet the output frequency does not change. The active microwave cavity has a cylindrically shaped window (41) located at the back-end of the cavity which extends inward towards the region of high RF fields inside the cavity. A large, lossy, irradiated sample such as a finger can be inserted into or behind this window and analyzed for radiation damage.

8 Claims, 5 Drawing Figures 4,674,513

ACTIVE MICROWAVE CAVITY FOR ELECTRON PARAMAGNETIC RESONANCE (EPR) APPARATUS

The invention described herein may be manufactured used and licensed by or for the Government for governmental purposes without the payment to me of any royalties thereon.

TECHNICAL FIELD

The present invention relates to electron paramagnetic resonance (EPR) measurements and, more particularly, to a microwave amplifier having a high Q active microwave cavity for use in EPR measurements on large lossy samples.

BACKGROUND OF THE INVENTION

An urgent need exists for a rapid, real-time determination of radiation damage to a person who has been exposed to gamma and/or neutron radiation.

It is well known that radiation breaks bonds between atoms in molecules. When the bonds are broken homolytically, free radicals result. When the bonds are broken heterolytically (diamagnetic), ionic fragments result. The free radicals, unlike ionic fragments, can be seen by EPR. Therefore, the technique for determining radiaion damage to a person by use of EPR is based on the amount and type of free radicals that are generated due to the radiation exposure. It has been suggested by experts in this field that a finger or tooth are potentially good constituents of the human body to utilize for performing EPR measurements to determine the extent of radiation damage. The free radicals, for example, in the bone, resonate when exposed to radio frequency (RF) photons in the X-Band (6.2-10.9 gigahertz (GHz)). A currently used method of exposing the sample that is to be analyzed to microwave energy is to place the sample in a passive, high Q-factor microwave cavity. The inside cross-sectional dimensions of an X-band cavity or waveguide are typically 0.4 by 0.9 inches for the 8.2 to 12.4 GHz frequency range. An X-Band rectangular cavity would have a length equal to an integral number of one-half waveguide wavelengths. One can easily see from these dimensions that a finger would occupy a considerable part of the cavity volume. This being the case, there exists a serious technical barrier (excessive loss that reduces the cavity factor) to overcome before a finger can be utilized as the sample to be analyzed for radiation damage by EPR. A finger, being large and dielectrically lossy, will load down a high Q-factor passive microwave X-Band cavity to a significant degree so that the EPR sensitivity will be drastically reduced, inhibiting any satisfactory measurements. In addition, a small frequency shift will occur which further reduces sensitivity.

SUMMARY OF THE INVENTION

It is a primary object of the present invention to provide a microwave cavity for EPR measurement apparatus which will enable one to determine the radiation damage of a large, lossy sample such as a human finger.

The above and other objects are achieved in accordance with the present invention wherein a microwave amplifier has an active microwave cavity which can be advantageously utilized to permit a sample of large size (<50 milliliter) to be analyzed in an X-Band active cavity. The RF energy is transported into the cavity by an electron beam carrying an amplified RF wave. The RF wave is essentially "trapped" in the cavity because of the non-reciprocal nature of the electron beam medium and because the guide at the input to the cavity has dimensions such that the frequency of the RF microwave energy is below the guide's lower cut-off freqency. The "trapped" RF energy in the cavity generates large, narrow resonant peaks in the cavity and a cavity Q-factor greater than 1000 can be realized, which is desirable for EPR measurements. In addition, a unique output frequency "locking" effect occurs in the output cavity due to a beam wave-to-beam wave interaction that takes place before the electron beam carrying the RF energy enters the output cavity. The input frequency can be varied from 1-2% yet the output frequency does not change. This feature is particularly advantageous since dielectric loading of a cavity has heretofore caused a small frequency change and thus a reduction in the Q-factor. Hence, this frequency "locking" effect increases the sensitivity of EPR measurement apparatus. The active X-Band microwave cavity has a cylindrically shaped window located at the backend of the cavity that extends inward towards the region of high-RF fields inside the cavity. A large, lossy, irradiated sample such as a finger can be inserted into or behind this window and analyzed for radiation damage. EPR apparatus, incorporating this active microwave cavity, gives a rapid, real-time means for determining radiation damage to a person.

BRIEF DESCRIPTION OF THE DRAWINGS

The invention will be more fully appreciated from the following detailed description when the same is considered in connection with the accompanying drawings, in which.

DETAILED DESCRIPTION

Figure 1:
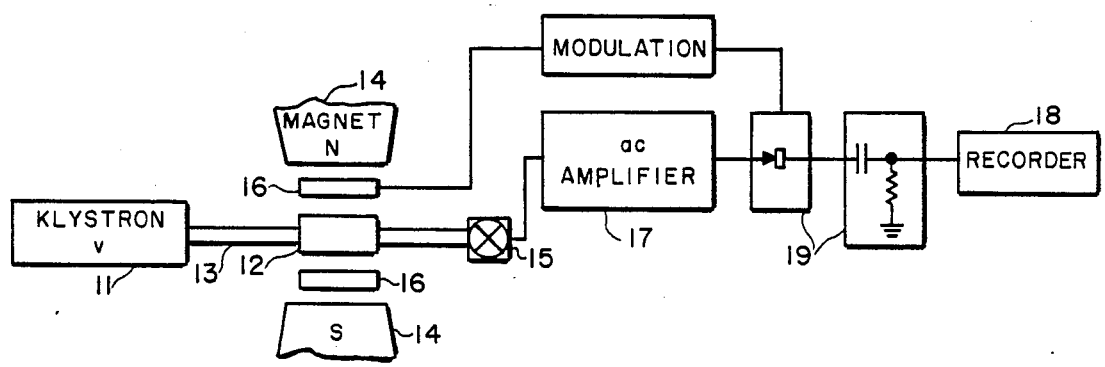
FIG. 1 is a schematic block diagram of a typical, prior art EPR instrument.

Turning now to FIG. 1 of the drawings, a typical, prior art, EPR instrument uses a microwave source 11 such as a klystron to generate low level (e.g., tens of watts) microwave power at the desired frequency, which is transmitted to a passive microwave cavity 12 by a conventional wave guide 13 or even coaxial cable. The microwave cavity has a Q-factor with a typical value of about 1500. The cavity is placed between the pole pieces 14 of an electromagnet which produces a dc magnetic field of typically 2 to 4 kilogauss. A microwave-crystal detector 15 is utilized to detect a low-power (30 milliwatts) RF signal from the output of the microwave cavity 12. Small modulation coils 16 are placed on both sides of the passive microwave cavity, between the cavity and pole pieces of the electromagnet. These coils add a small (tens of gauss) oscillating magnetic field to the large dc magnetic field. The resultant $H_o + H$ modulation swings back and forth, alternately increasing and decreasing the absorption height. The dc also alternately increases and decreases, which provides an ac to be amplified in ac amplifier 17, and rectified and phase detected by a phase sensitive rectifier filter 19. The resultant signal is then recorded by recorder 18, which may comprise a conventional amplitude vs. time recording device. The amplified ac allows one to see the small absorption of the microwave power on top of the large dc due to the EPR signal. The swing of the modulation field produces the observed derivatives of absorption lines. The EPR instrument shown in FIG. 1 can routinely analyze, at X-Band, lossy samples with volumes of a few microliters. However, large, lossy samples with volumes of several (e.g. 50) milliliters, such as a finger, cannot be analyzed with this conventional prior art EPR instrument for resonating free radicals at X-Band frequencies. The inability to analyze large, lossy samples using passive X-Band cavities was the impetus for investigating the use of a new and different microwave cavity to circumvent this problem or shortcoming.

The prior art EPR instrument shown in FIG. 1 is illustrated on page 205 and described on pages 205–207 of the text by M. Bersohn and J. Bird, entitled "Electon Paramagnetic Resonance," W. Benjamin Inc. (1966).

Figure 2:
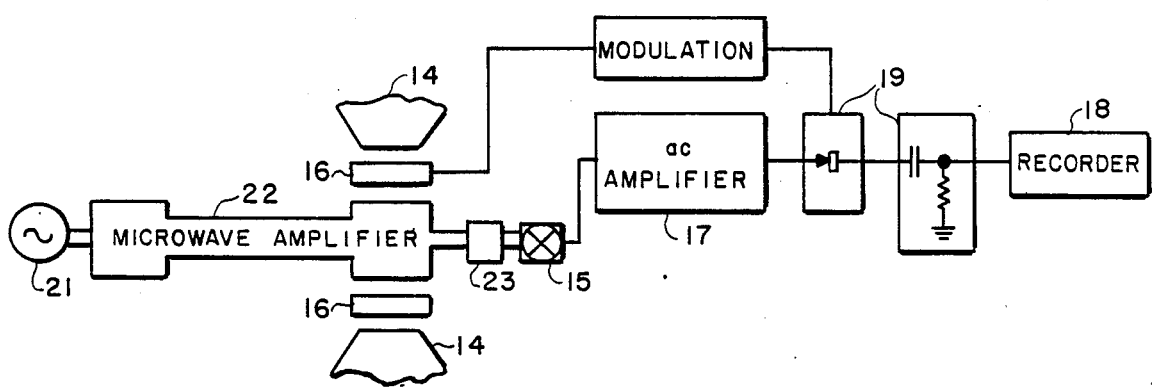
FIG. 2 is a block diagram of an EPR instrument which incorporates a microwave amplifier having an active microwave cavity in accordance with the present invention.

The active microwave cavity of the present invention, unlike the prior art passive microwave cavity, uses an electron beam to input RF energy into the cavity. This being the case, the active microwave cavity is (and must be) under vacuum. FIG. 2 is a block schematic diagram showing the components of EPR apparatus which incorporatess a microwave amplifier that has an active microwave cavity. The klystron and the passive microwave cavity of FIG. 1 are replaced by a solid-state RF driver 21, operating at a frequency of about 10 GHz, and a microwave amplifier 22. The output section of the amplifier 22 is the active microwave cavity. One additional component is shown in FIG. 2, i.e., a dc inner block 23, the purpose of which will be explained hereinafter. The remaining components shown in FIG. 2 are similar to their counterparts shown in FIG. 1.

Figure 3:
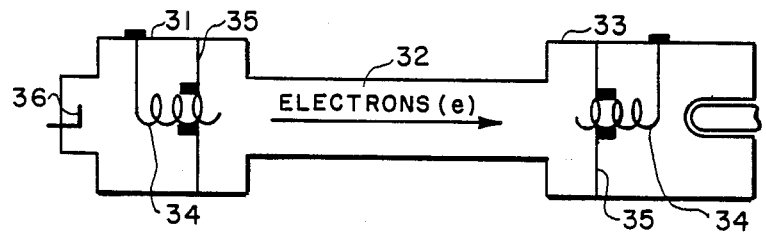
FIG. 3 is a simplified schematic diagram of the space-charge microwave amplifier.

FIG. 3 shows the microwave amplifier of the invention in greater detail. The amplifier 22 comprises an input section 31 a drift section 32, and an output section 33. In the preferred embodiment of the invention, the microwave amplifier 22 is cylindrical; however, it will be evident to those in the art that the invention is not limited to cylindrical sections. For X-Band operation the input and output sections are 1.5 inches in diameter, and the drift section has a diameter of ⅝ of an inch. The input section is 4 inches in length, the drift section is 6 inches long, and the output section has a length of 5 inches. These dimensions are given only by way of example and, here again, the present invention is clearly not limited to a microwave amplifier of exactly these dimensions.

The input and output sections 31 and 33 have small (e.g., 3–10 turns) helical couplers 34 for coupling RF energy onto and off of the electron beam. The couplers are supported in their respective sections by the helix supports 35. A conventional Pierce type electron gun 36 is used, which has a heater and a thermionic cathode. The drift section 32 of the tube is designed so that the frequency of operation is below the lower cut-off frequency of the guide. This is an important feature of the invention, and it has been verified experimentally that the RF energy can only be transmitted to the output section when the electron beam is on. In addition, this is a non-reciprocal effect. The phase velocity of the RF wave on the electron beam is, and must be, in the same direction as the drift velocity of the electron beam in order to transport energy from input to output sections. This is achieved by properly inputting the RF into the path of the electron beam, in the manner indicated in FIG. 3, and also by a tight winding of the input helix so that we operate on the forward wave of the helix. The backward wave of the helix can also be utilized by loosely winding the helix and inputting the RF energy on the end of the helical coupler 34 furthest from the pierce gun 36. The RF wave travels on the beam medium in drift section 32, is amplified by a beam wave-to-beam wave interaction, and is coupled onto output helical coupler 34 in output section 33. Thus, once the RF energy is in the output section of the tube, it cannot return back towards the drift region. In essence, the RF energy becomes "trapped" in the output cavity and large resonances are produced.

Figure 5:
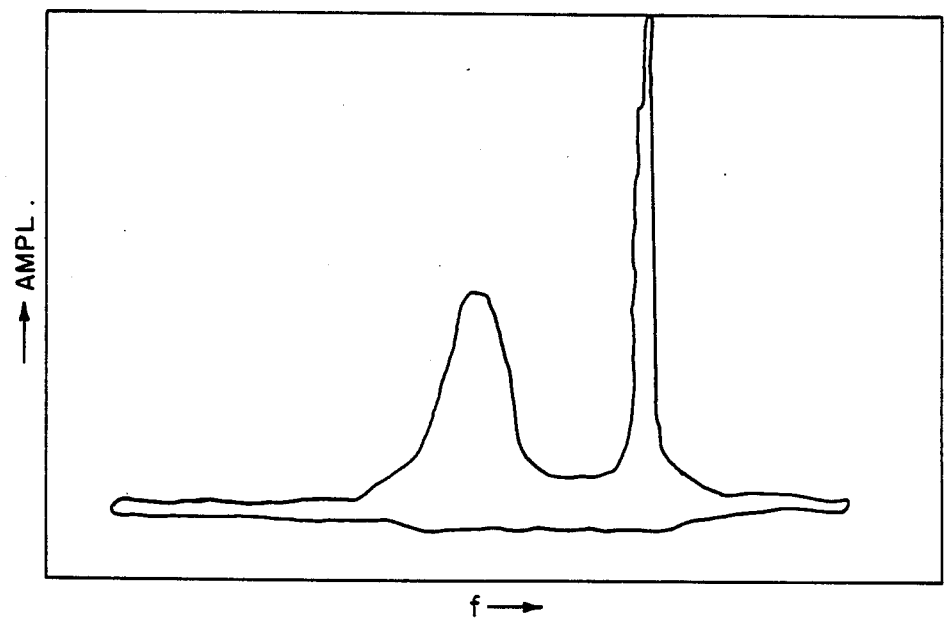
FIG. 5 is a trace of a spectrum analyzer picture of typical output and input RF signals of the microwave amplifier of the invention.

Another important feature of this active microwave cavity is that the RF signal in the output cavity is insensitive to small input frequency changes of about 1 to 2%. This output frequency "locking" effect has been demonstrated in a series of spectrum analyzer pictures which were obtained as the input frequency was varied from 6.742 GHz to 6.710 GHz. FIG. 5 illustrates just one of these spectrum analyser pictures. The narrow pulse is the input frequency pulse and the wide pulse is the output frequency pulse from the microwave cavity. In the demonstration the input frequency wave varied over the given range, but the output signal did not change in frequency. It is not evident from FIG. 5 but the output pulse power is substantially greater than the input pulse power. The input signal is a continuous wave signal sampled before entering the amplifier. The output signal is a small RF duty ($\approx 1\%$) pulse that could have a power gain of 50 dB.

The consequence of the output frequency "locking" is that once the amplifier is tuned to resonance, any small change in frequency normally due to dielectric loading in the output section will not take place. A large, lossy sample can be placed in close proximity to large electromagnetic fields in the cavity without causing a serious degradation to the Q of the cavity. This is a significant characteristic of the active microwave cavity since the sensitivity of EPR measurements will be enhanced. It should be noted that this frequency "locking" effect does not occur with conventional space-charge wave amplifiers, such as a traveling-wave tube (TWT). Unlike the conventional TWT, where an electron beam gives up energy to a circuit wave produced by RF currents traveling on a continuous helix structure, this amplifier involves a beam wave-beam wave interaction. That is, a space-charge wave of the electron beam interacts with a transverse wave of the electron beam. The small helical couplers 34, of FIG. 3, are not important for achieving the high gain of the microwave amplifier, but primarily serve to couple energy onto and off of the electron beam. The beam wave-beam wave interaction takes place in the drift section of the amplifier. Therefore, the electron beam enters the output section carrying an amplified RF wave.

Figure 4:
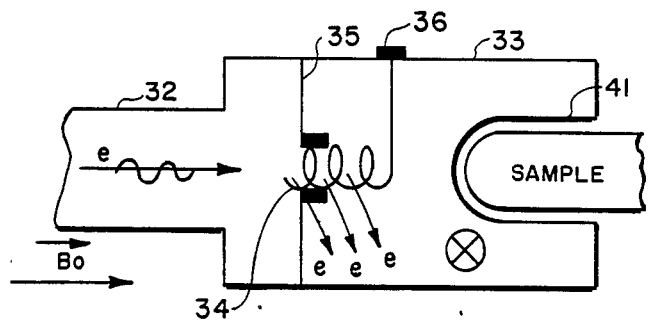
FIG. 4 is an expanded view of the active microwave cavity.

FIG. 4 is an expanded view of the active microwave cavity, the output section of the microwave amplifier. The electron beam in the input and drift regions is focussed by means of an axial magnetic field ($\overline{B_0}$) produced by a permanent magnet structure. The output section of the tube is placed between the pole pieces of an electromagnet (see FIG. 2) and, therefore, does not have a permanent magnet structure as does the input and drift sections. The electron beam (e) begins to spread as it enters the output section and will strike the helical coupler 34 and the side wall of the cavity because of the magnetic field generated between the pole pieces of the electromagnet. The direction of the magnetic field generated by the electromagnet is indicated by ⊗ in FIG. 4. The ⊗ inplies a direction into the plane of the paper. The helical coupler and the tube body serves as collectors. The electron beam, as it attempts to pass through the helical coupler 34, will induce RF currents on the helix and give up its RF energy. This induced RF energy is coupled to the outside environment via an RF vacuum window 36. The energy collected on the side wall of the cavity is not used and simply dissipates in the side wall. The dc inner block 23, shown in FIG. 2, will block the dc current collected on the helix due to beam interception. A large, lossy sample (such as a finger) to be analyzed is placed in close proximity to the large RF fields by using a window 41 made of quartz, sapphire, or other suitable material which will allow RF energy to transmit though it. The lossy, irradiated sample is placed into or behind the window, as shown in FIG. 4, and will absorb microwave energy due to resonating free radicals and due to dielectric loading. As will be appreciated by those in this art, the greater the number of resonating free radicals, the greater the absorption of the RF microwave energy.

Important design parameters are given in the table below, for the active microwave amplifier, and for X-Band operation. These operating parameters would, of course, change for operation in different frequency bands. Typical physical dimensions for the X-Band microwave amplifier, including the X-Band output cavity, have been given heretofore.

TABLE
Design Parameters For An X-Band Amplifier

| | | | |
|---|---|---|---|
| Beam Voltage | 5 Kilovolts (KV) | Power Output | <50 Watts |
| Beam Current | 100 Milliamperes (MA) | RF Gain | 40 to 50 dB |
| Efficiency | 10% | Operation Mode | CW or Pulsed (low duty cycle) |
| Bandwidth | 1-2% | Focussing | Permanent Magnet |

EPR measurements for analyzing radiation damage, by observing the free radicals in the bone, would be conducted at a frequency of about 10 GHz. At the 10 GHz frequency, a Q-valve greater than 1000 is attainable for an optimized, active microwave cavity.

While it may seem to be somewhat redundant, it perhaps could prove advantageous if the foregoing disclosure is now summarized and somewhat rephrased. A microwave X-Band amplifier having an active microwave cavity has been disclosed, which can be used in an EPR instrument for analyzing radiation damage of a large, lossy sample such as a finger of a person. The microwave cavity has important characteristics which permit a sample of large size (50 milliliters or more) to be analyzed in an X-Band cavity. The RF energy is transported into the cavity by an electron beam carrying an amplified RF wave. The RF wave is essentially "trapped" in this cavity because of the non-reciprocal nature of the electron beam medium and because the guide at the input to the cavity has dimensions such that the frequency of the microwave energy is below the guide's lower cut-off frequency. The "trapped" RF energy in the cavity generates large resonant peaks and a Q-factor of 1000 or more is attainable. Also observed is a unique output frequency "locking" effect that occurs in the output cavity resulting from a beam wave-beam wave interaction in the drift section. The input frequency can be varied from 1-2% and the output frequency does not change. This particular characteristic is beneficial since dielectric loading of a cavity generally causes a small frequency change and a reduction in the Q-factor. The frequency "locking" effect will increase the sensitivity of the EPR measurements.

The active X-Band microwave cavity has a cylindrically shaped RF window located at the back-end of the cavity that extends inward towards the region of high-RF fields inside the cavity. A large, lossy, irradiated sample such as a finger can be inserted behind this window and analyzed for radiation damage. The EPR instrument, with the active microwave cavity, gives a rapid, real-time means for determining radiation damage to a person. Another potential application is for determining the dielectric constant of a material. Also, the active microwave cavity has a potential use for ferrimagnetic resonance measurements and for analyzing mammalian tissues and their relation to pathology.

Various modifications of the disclosed invention should be readily apparent to those skilled in this field. For example, in lieu of the driver and amplifier, an oscillator could be utilized. Accordingly, it will be obvious at this time that the above-described microwave amplifier having an active microwave cavity is merely illustrative of the application and of the principles of the present invention, and numerous modifications thereof may be devised by those skilled in the art without departing from the spirit and scope of the invention.

What is claimed is:

1. A microwave amplifier for use in electron paramagnetic resonance (EPR) measurement apparatus comprising an input section, a drift section, and an active microwave cavity forming an output section, means for inputting an axial electron beam into said microwave amplifier, a pair of small helical couplers mounted in the input and output sections, respectively, for coupling RF microwave energy onto and off of the electron beam, said drift section having dimensions such that the frequency of the microwave energy is below the lower cut-off frequency of the drift section, said output cavity being insensitive to small input frequency changes, and a cylindrically-shaped window located at the back-end of the cavity and extending inward towards the region of high RF fields inside the active cavity.

2. A microwave amplifier as defined in claim 1 including driver means for generating the RF microwave energy, and means for coupling the RF microwave energy from said driver means to the helical coupler in said input section.

3. A microwave amplifier as defined in claim 2 wherein said driver means is a solid-state device which operates at a predetermined frequency in the X-Band.

4. A microwave amplifier as defined in claims 3 including means for establishing a phase velocity of the RF wave on the electron beam in the same direction as the drift velocity of the electron beam.

5. A microwave amplifier as defined in claim 4 wherein said window is adapted to receive a large, lossy, irradiated sample such as a human finger, said microwave amplifier being maintained under vacuum.

6. A microwave amplifier as defined in claim 5 wherein the input, drift, and output sections are cylindrical.

7. A microwave amplifier for use in electron paramagnetic resonance (EPR) measurement apparatus comprising an input section, a drift or intermediate section, and an active X-Band microwave cavity forming an output section, said microwave amplifier having an electron gun for producing an electron beam, means for establishing an axial travel of said electron beam in the input and drift sections of said microwave amplifier, a pair of small helical couplers mounted in the input and output sections, respectively, for coupling microwave energy onto and off of the electron beam, solid stae RF driver means for generating RF microwave energy, means for coupling said RF microwave energy from said driver means to the helical coupler in said input section, said driver means operating at a predetermined frequency in the X-Band, said drift section having dimensions such that the frequency of the RF microwave energy is below the lower cut-off frequency of the drift section, said output cavity being insensitive to small input frequency changes, means for establishing a phase velocity of the RF wave on the electron beam in the same direction as the drift velocity of the electron beam so as to transport energy from the input to output sections, and a cylindrically-shaped window made of a material that permits RF energy to pass through it, said window being located at the back-end of the cavity and extending inward towards the region of high RF fields inside the active cavity, said window being adapted to receive a large, lossy, irradiated sample such as a human finger.

8. A microwave amplifier as defined in claim 7 including dc inner block means coupled to the helical coupler in the output section of the microwave amplifier for blocking dc current collected on the helical coupler due to electron beam interception.

* * * * *